United States Patent [19]
Mansouri

[11] Patent Number: 6,099,849
[45] Date of Patent: Aug. 8, 2000

[54] SKIN CARE MOISTURIZERS AND CLEANSERS

[76] Inventor: Zari Mansouri, 828 Port Walk Pl., Redwood Shores, Calif. 94065

[21] Appl. No.: 09/026,016

[22] Filed: Feb. 19, 1998

Related U.S. Application Data

[62] Division of application No. 08/487,242, Jun. 13, 1995.

[51] Int. Cl.[7] ........................................ A61K 7/00
[52] U.S. Cl. .......................... 424/401; 424/404; 424/70.1; 424/74; 501/1; 501/11; 501/32; 514/721; 514/724; 514/737
[58] Field of Search ..................... 424/401, 70.1, 424/404, 74; 514/721, 724, 737; 501/1, 11, 32

[56] References Cited

U.S. PATENT DOCUMENTS

| | | | |
|---|---|---|---|
| 4,737,360 | 4/1988 | Allen et al. | 424/60 |
| 4,847,078 | 7/1989 | Sheppard et al. | 424/80 |
| 5,137,875 | 8/1992 | Tsunewaga | 514/21 |
| 5,254,334 | 10/1993 | Ramirez et al. | 424/70 |
| 5,279,824 | 1/1994 | Sawyer . | |
| 5,296,158 | 3/1994 | MacGlip et al. | 252/108 |
| 5,416,075 | 5/1995 | Carson et al. | 514/23 |
| 5,417,875 | 5/1995 | Nozaki | 252/106 |
| 5,442,053 | 8/1995 | Della Valle | 536/55.1 |
| 5,762,950 | 6/1998 | Yli-Urpo et al. | 424/422 |

FOREIGN PATENT DOCUMENTS

| | | |
|---|---|---|
| 0 496 434 | 7/1992 | European Pat. Off. . |
| 1096-104A | 10/1987 | Japan . |
| 1196-806A | 10/1987 | Japan . |
| 61-116137 | 5/1988 | Japan . |
| 2029-497A | 7/1988 | Japan . |
| 61-170785 | 7/1988 | Japan . |
| 61-282573 | 11/1988 | Japan . |
| 1186-814A | 7/1989 | Japan . |
| 62-254415 | 7/1989 | Japan . |
| 3103-608A | 9/1989 | Japan . |
| 2-141013 | 5/1992 | Japan . |
| 4-219321 | 6/1994 | Japan . |
| 7-109217 | 4/1995 | Japan . |
| 2 048 670 | 12/1980 | United Kingdom . |
| 2 274 588 | 1/1994 | United Kingdom . |

OTHER PUBLICATIONS

Smith, R.G. & Lee, S.A., "Large–scale Isolation and Partial Purification of type C RNA Viruses on Hydroxyapatite," *Analytical Biochemistry* (1978) vol. 86:252–263.

Tsuru, S. et al., "Adsorption and Preparation of Human Viruses Using hydroxyapatite Column," *Journal of Biomedical materials and Engineering*, (1991) vol. 1.

Tsuru, S. et al., "A Rapid Method For The isolation of Functional Human T Lymphocytes Using Hydroxyapatite Column Fractionation," *J. Immunological Methods* (1988) vol. 106:169–174.

Let's Get Clinical (Medicated Skin Care Sector now make up 8% of total UK skin care market & will continue to grow despite fall in teenage population) *Chemist & Druggist* (Feb. 11, 1995) vol. 5970:224.

"Relaunch for Cuticura Announces relaunch of Cuticura Hygiene Plus range of reformulated," *Chemist & Druggist* (Sep. 24, 1994) P.482.

"Cuticura Medicated Foam Wash Manufacturer: Dep. Corp. Category: Medicated Skin Care," *Product Alert* (Jan. 13, 1992) p. N/A.

"Colgate–Palmolive Launching Softsoap Anti–Bacterial Moisturizing Soap and Shower Gel," *FDC Reports Rose Sheet* (Aug. 7, 1989) p. 7.

American International Chemical's Product Information/Sales Brochure: "Pentax Ceramic hydroxyapatite," (No date found).

Gorbunoff, M.J. & Timasheff, S.N., "The Interaction of Proteins With Hydroxyapatite," *Analytical Biochemistry* (1984) vol. 136:440–445.

Josic, D. et al., "Purification of monoclonal Antibodies By Hydroxyapatite HPLC and Size Exclusion HPLC," *Biol. Chem. Hoppe–Seyler* (1991) vol. 372:149–156.

Kadoya, T. et al., "A New Spherical Hydroxyapatite For High Performance Liquid Chromatography of Proteins," *J. Liquid Chromatography* (1986) vol. 9:3543–3557.

Kadoya, T. et al., "High Performance Liquid Chromatography of Proteins On A Hydroxyapatite Column," *J. Liquid Chromatography* (1988) vol. 11:2951–2967.

Kasai, R. et al., "High Performance Liquid Chromatography of Glycosides On A New Type of Hydroxyapatite Column," *J. Chromatography* (1987) vol. 407:205–210.

Kawasaki, T. et al., "Hydroxyapatite High Performance Liquid Chromatography: Column Performance Of Proteins," *European Journal Biochem.* (1985) vol. 152:361–371.

Laboratory Skin Care, Inc. (LSC), *Product Data Sheet*.

Macro–PrepR Ceramic hydroxyapatite, BIO–RAD Data Sheet C–100.

Ogawa, T. et al., "Normal Phase High Performance Liquid Chromatography of Glycosides On A New Ceramic Hydroxyapatite Beads Column," Asahi Optical Co., Ltd. Poster Presentation at CLC, Stockholm, Jun. 25–30, 1989 (Text and Figures).

Poster Presentation at the 7th International Congress of Immunology,Berlin, Jul. 29–Aug. 5, 1989, (Text and Figures), "Pentax Cell Column for Isolation of Human T–Lymphocytes,".

*Primary Examiner*—Thurman K. Page
*Assistant Examiner*—Lakshmi Channavajjala
*Attorney, Agent, or Firm*—Bozicevic, Field & Francis; Bret Field

[57] ABSTRACT

Methods of using absorption enhancer as a component of skin care compositions for moisturizing and protecting the skin. Antimicrobial skin care compositions for cleansing and moisturizing the skin, comprising an absorption enhancer, an antimicrobial function enhancer and bound lipid removals, humectants, emollients and extracts of botanical herbs. Methods for preparing skin care compositions comprising an absorption enhancer.

8 Claims, No Drawings

SKIN CARE MOISTURIZERS AND CLEANSERS

This application is a Divisional of application Ser. No. 08/487,242, filed Jun. 13, 1995.

BACKGROUND TO THE INVENTION

1. Field of the Invention

The invention relates generally to a method of making skin care products and to methods of using such products. This invention also relates to skin care products which moisturize the skin and prevent excessive drying of the skin.

This invention further relates to skin care products which are antimicrobial and help prevent infection by pathogenic microorganisms, and which mitigate against the spread of such pathogens.

In particular, the invention is concerned with formulations for cleansing and moisturizing skin which are antimicrobial, alcohol-free, contain no animal- or petroleum-based products, have a water base, and comprise an absorption enhancer to promote rapid uptake of the formulation by the skin.

This invention still further relates to skin cleansing products which are antimicrobial, and non-irritating and non-drying to the skin after frequent use. The instant invention further relates to skin moisturizing products which are non-greasy, which rapidly penetrate the outer layers of the skin, and which form a shield to prevent loss of moisture from the skin and to shield from exposure of chemicals and detergents commonly found in health/industry works.

2. Background of the Related Art

Excessive drying of the skin is a common problem which is often the result of exposure to wind, sun and low humidity, or a combination of these factors. Frequent washing of the hands can also result in excessive drying. This is particularly true if abrasive soaps, alcohol-based products and other harsh chemicals are used for cleansing.

Skin that has been excessively dried is not only unsightly, but also tends to slough off excessively and to crack, leading to abrasions of the skin surface. Because the skin serves a key role as a physical barrier to the entry of parasites and pathogens, excessive drying can lead to a breach of the barrier and infection by pathogenic bacteria and fungi. Thus cracks or openings in the skin serve as a portal of entry for pathogens and potential pathogens. Even organisms that are normally considered to be non-pathogens can result in opportunistic infection in immunologically compromised individuals. Infections may be mild or severe and may be localized to the initial site(s) of infection or may be systemic and spread throughout the body. Such spread may occur by direct extension to contiguous tissues, or by way of the lymphatics and ultimately by way of the bloodstream.

Thus, the frequent application of many prior art skin cleansing compositions contributes to skin damage, and therefore may indirectly increase the risk of skin infections. Many prior art skin moisturizers contain petroleum products which dissolve latex gloves as worn by workers in diverse fields, including the health care field.

Similarly, many prior art moisturizers contain animal-derived products, such as lanolin. It is known that certain animal-derived products may cause skin allergies and/or dermatitis.

Skin care products of the instant invention allow for frequent use of the products to protect the skin and prevent damage due to drying. In so doing, skin care products under the invention help to prevent infection of the skin itself and entry of pathogens through the skin where they may infect underlying tissues.

Skin cleansing products of the instant invention are formulated not only to accommodate continued frequent use without causing drying and cracking of the skin but also, by the inclusion of one or more antimicrobial agents, to prevent the transmission and spread of pathogenic or potentially pathogenic microorganisms.

Skin care products of the instant invention are formulated to promote the absorption of the composition by the skin. In particular, skin care products of the instant invention comprise an absorption enhancing material. The absorption enhancing material of choice under the invention is a form of ceramic hydroxyapatite. Ceramic hydroxyapatite under the invention is in the form of macroporous spheres of predetermined size range, and is chemically pure. It is formed by the agglomeration of crystals of hydroxyapatite, of 0.5 to 1.0. micrometer size range, into spherical particles which are then sintered at high temperature to provide mechanically stable spheres, Ceramic hydroxyapatite which is useful in the practice of the instant invention is exemplified by that manufactured by the Asahi Optical Company, Tokyo. Ceramic hydroxyapatite has been widely used as a chromatographic separation medium (see, for example, R. Kasai et al. *J. Chromatography* 407, 205 (1987); S. Tsuru et al. *J. Immunol. Methods* 106, 169 (1988); T. Kadoya et al. *J. Liquid Chromatography* 9,3543 (1986); T. Kadoya et al. *J. Liquid Chromatography* 11,2951 (1986).

Apart from ceramic hydroxyapatite referred to above, hydroxyapatite has been produced in several other forms, each with a characteristic particle morphology, size distribution and surface structure, as observed by scanning electron microscopy (T. Kadoya et al. *J. Liquid Chromatography* 9,3543 (1986).

Hydroxyapatite has also been ascribed various non-chromatographic applications. For example, JP 254415 discloses cosmetic materials containing spherical hydroxyapatite. JP 266066 teaches a melanin-lightening composition including ethyl alcohol and sodium hydroxide. JP 007409 teaches the use of hydroxyapatite for the selective removal of protein from the body surface. JP 179074 discloses the use of hydroxyapatite as an abrasive, to assist in the cleaning of inanimate surfaces. JP 238429 discloses a blending agent, comprising polystyrene beads coated with hydroxyapatite.

SUMMARY OF THE INVENTION

Skin moisturizing products of the present invention are formulated to protect the skin and maintain the skin in a healthy condition. Skin moisturizing products of the present invention are also formulated to be antimicrobial, thereby further reducing the risk of infection by pathogens. Furthermore, the antimicrobial properties of moisturizing products of the invention reduce the risk of transmission of pathogenic and potentially pathogenic microorganisms. Skin care products of the instant invention are further formulated to rapidly penetrate the skin, whereby active ingredients of the formulation are more effective.

The compositions and methods of the instant invention may be used to protect the integrity of the skin. The compositions and methods of the instant invention may also be used to promote and maintain healthy skin. The skin cleansing compositions of the instant invention may be used frequently to prevent the spread of pathogenic or potentially pathogenic microorganisms. The skin cleansing compositions of the instant invention may also be used frequently on a continual basis with minimal risk of causing drying, irritation, inflammation, or damage to the skin. The skin moisturizing compositions of the instant invention may be used to minimize the risk of irritation and infection. The skin cleansing and moisturizing products of the instant invention do not dissolve latex and are fully compatible with the use of latex gloves. Thus, the skin moisturizing compositions of the instant invention may be used with latex gloves without the risk of dissolution of the latex or other damage to the latex barrier.

The methods and compositions of the invention may further be used to promote the rapid absorption of biologically active components by the skin. In accordance with one embodiment of the invention, the skin moisturizer composition may be used as a single application, or application may be repeated periodically over an extended time period as needed.

In accordance with another method of the invention, a skin moisturizing composition, under the invention, may be applied specifically or preferentially to the point or area of a minor cut, crack, or abrasion of the skin. Such application may protect the epidermis and the dermis from further damage or infection of the skin.

DETAILED DESCRIPTION OF THE INVENTION

The skin or integumentary system is an essential, physiologically and anatomically specialized boundary lamina. It covers the entire external surface of the body. The total area of skin in an adult is between 1.2 to 2.2 m2, and comprises about 10% of the total body mass, making it the largest organ of the human body. Functionally, the skin acts as an interface between the internal and external environment, and fulfills thermo regulatory, sensory, and other functions, as well as playing a key role as a highly effective physical barrier against infectious agents and dehydration. The skin also acts as a barrier against mechanical, chemical, osmotic, thermal and photic damage.

The condition of the skin is generally considered, by medical practitioners and lay people alike, to reflect the state of health, age and other aspects of life of an individual.

Histologically, three major tissue layers are identified. The uppermost layer, the epidermis, is a relatively thin stratified squamous epithelium which is itself composed of five strata. Subjacent to the epidermis is the dermis, a dense fibroelastic connective tissue stroma. The third layer, lying beneath the dermis is the subcutaneous layer composed of areolar and fatty connective tissue.

There are three basic cell types in the epidermis: keratinocytes which produce keratin, melanocytes which are involved in pigmentation, and Langerhans cells which aid the immune system by intercepting foreign bodies in the skin. In the epidermis a mitotic layer at the base provides keratinocytes which continuously replace those shed at the skin surface.

The epidermis can be divided into layers according to the stage of maturation of keratinocytes within it. These layers are, from deep to superficial, as follows: stratum basale, stratum spinosum, stratum granulosum, stratum lucidum and stratum corneum. The first three of these layers are metabolically active, while the two upper layers which have attained terminal keratinization constitute the cornified zone. Cells of the stratum corneum eventually become detached from the epidermal surface and are replaced from below. Typically the time taken for a newly-formed keratinocyte to pass to the surface and be shed ranges from 45–75 days.

However, under certain pathological conditions of the skin, turnover rates are much higher. As a result keratinization is incomplete and the normal barrier functions of the skin are lost.

The dermis comprises a strong yet flexible layer which consists primarily of collagen. This layer, which contains nerves, blood vessels, hair follicles, sebaceous glands and apocrine glands, fulfills vital roles in thermoregulation and sensory perception. The sebaceous glands produce sebum, a natural lipid material which helps to prevent drying, cracking and excessive shedding of the outer layers of the skin.

Compositions for cleansing and moisturizing the skin according to the invention comprise an antimicrobial agent, an emollient and an absorption enhancer in combinations as described below.

i. Antimicrobial component

The present invention provides skin cleansing and moisturizing compositions, comprising a chemical antimicrobial agent which functions to inhibit the growth of pathogenic or potentially pathogenic bacteria and fungi, or to kill such organisms. Thus the chemical antimicrobial agent may be bacteriostatic, bacteriocidal, fungistatic or fungicidal in its action.

A preferred chemical antimicrobial agent for use under the invention is Triclosan. This agent used in the formulation has been found effective against the whole genera of microoranisms, (for example: bacteria, fungi, *pseudomonas aeruginosa, pseudomonas capacia, staphylococcus aureus, escherichia coli, candida albicans, aspergillus niger, salmonella typhimurium*, etc . . . ). Apart from its role in preventing infection via the skin and in preventing the spread and transmission of pathogenic microorganisms, the antimicrobial component of the composition also inhibits the growth of spoilage organisms during storage of the product. The antimicrobial chemical agent is normally present in an amount of from 0.001–5% by weight, preferably from 0.05–2% by weight, and more preferably from 0.1–1% by weight.

ii. Water activity depressant

Compositions according to the invention may also comprise one or more water activity depressants, the function of which is, in part, to inhibit the growth of microorganisms during product storage and to preserve the product. Water activity depressants, with or without the inclusion of an antibiotic chemical, help to prevent the growth of spoilage organisms. Examples of water activity depressants include sorbitol, propylene glycol, sugars, and alkali metal salts, including carboxylates, halides, and sulfates. A preferred water activity depressant is sorbitol. The sorbitol component of the composition is preferably present in a concentration of from 1–20% by weight, more preferably from 1–10% by weight, and most preferably from 1–2% by weight.

iii. Absorption carrier for carrying out the function of absorption (sometimes referred to as absorption enhancer below it being understood that these materials do not enhance absorption but actually carries out the function of absorption).

Compositions under the invention also comprise one or more absorption carrier. The function of such an absorption carrier is, in part, to promote the uptake of the product by the skin. Uptake of the product prevents excessive loss of the product from the skin surface and promotes product contact with the metabolically active cells of the dermis and epidermis beneath the cornified zone of the stratum lucidum and stratum corneum.

A preferred absorption carrier is ceramic hydroxyapatite. Ceramic hydroxyapatite functions as an unbound/excess lipid remover and anti-microbial function enhancer. Ceramic hydroxyapatite used under the invention is a form of chemically pure calcium phosphate (molecular formula $Ca_{2+10}(PO_4^{3-})_6(OH)_2$ which is produced as spheres with a controlled diameter. Preferably the median diameter of ceramic hydroxyapatite under the invention is in the range of 1–10 micrometers, more preferably in the range of 2–5 micrometers.

Ceramic hydroxyapatite spheres are manufactured by the agglomeration of small crystals (50–100 nm size range) followed by sintering at high temperature. As a result of this process, each sphere is porous and can act as a miniature sponge. This characteristic of ceramic hydroxyapatite spheres allows it to absorb, carry, and subsequently release components of the composition with which it has been formulated.

Ceramic hydroxyapatite having a mean particle diameter in the range of 2–6 micrometers can act as an efficient absorption and spreading agent for liquid phase materials. The carrier and absorption enhancing properties of ceramic hydroxyapatite is due to both its porosity and its affinity for various substances. For example, ceramic hydroxyapatite has the ability to bind water, charged molecules, lipids, proteins, and nucleic acids. The porous nature of ceramic hydroxyapatite allows it to bind and then slowly release a relatively large volume of liquid phase materials.

Due to the small spherical nature of the ceramic hydroxyapatite particles, it may also act as a lubricant. Conventional (i.e. non-ceramic) hydroxyapatite is known to bind to biological molecules, including proteins, lipoproteins, lipids and nucleic acids ((see, for example, D. Josic et al. *Biol. Chem. Hoppe-Seyler* 372, 149 (1991); K. J. Primes et al. *J. Chromatography*, 236, 519 (1982); S. Hjerten, *Biochim. Biophys. Acta*, 31, 216 (1959); G. Bernardi and W. H. Cook, ibid. 44, 96 (1960); R. K. Main et al. *J. Am. Chem. Soc.* 81, 6490 ((1959); A. Tiselius et al. *Arch. Biochem. Biophys. Acta* 65, 132 (1956)). However, in comparison to ceramic hydroxyapatite, conventional hydroxyapatite is produced as particles which are more irregular in shape and in size, and also more fragile. Ceramic hydroxyapatite is also superior to conventional hydroxyapatite in that ceramic hydroxyapatite spheres are resistant to high temperature and pressure, and are much more physically stable than conventional hydroxyapatite. (T. Kadoya et al. *J. Liquid Chromatography*, 9, 3543 (1986). This physical stability allows for the agitation or mixing of ceramic hydroxyapatite without disintegration of the particles. Ceramic hydroxyapatite is also more stable chemically than conventional hydroxyapatite, being stable for at least five years when stored at room temperature in dry or hydrated form.

Because hydroxyapatite binds lipids (K. Hobara et al., JOURNAL, YEAR (*REACTIONS OF HYDROXYAPATITE WITH LIPIDS*), and K. J. Primes et al. *J. Chromatography*, 236, 519 (1982)), ceramic hydroxyapatite, under the invention, may bind to lipid constituents of the instant compositions, as well as to lipid components of the skin. Ceramic hydroxyapatite has the additional advantage in the context of the present invention of binding to proteins much more strongly than does conventional hydroxyapatite. In binding to proteins of the skin, ceramic hydroxyapatite under the invention can act as a bridge between the proteins of skin cells and bound lipids. The resulting layer of bound lipid molecules can serve as an effective protective film to prevent dehydration of, and damage to, the skin.

Finally, ceramic hydroxyapatite, due to its propensity to bind to biological molecules, may bind to various surface components of microbial cells and promote the immobilization and inactivation of microorganisms.

Ceramic hydroxyapatite is preferably present in compositions under the invention at a concentration of from 0.001–10%, by weight, more preferably 0.01–5% by weight, and even more preferably from 0.05–1% by weight.

iv. Vehicle

The compositions according to the invention also comprise a liquid, solid or semi-solid physiologically and cosmetically acceptable vehicle or carrier. A suitable vehicle, under the invention, may act variously as solvent, diluent or dispersant for the constituents of the composition, and allows for the uniform application of the constituents to the surface of the skin at an appropriate dilution. It will be apparent to the skilled artisan that the range of possible vehicles is very broad. In general, compositions according to this invention may comprise water as a vehicle, and/or at least one physiologically and cosmetically acceptable vehicle other than water.

When water comprises a vehicle in compositions under the invention, preferably the water is deionized. Vehicles other than water that can be used in compositions under the invention may be liquids or solids, including emollients, various solvents, powders, and humectants. Carriers, including water, may be used singly or in combination. Suitable carriers may include, but are not limited to, the following examples:

water castor oil, ethylene glycol monobutyl ether, diethylene glycol monoethyl ether, corn oil, dimethyl sulfoxide, ethylene glycol, isopropanol, soybean oil, glycerin, soluble collagen, zinc oxide, titanium oxide, talc, Kaolin, hyaluronic acid.

The active constituents of the skin care compositions according to the invention may be soluble or insoluble in a liquid carrier. If the active constituents are soluble in the carrier, the carrier acts as solvent for the active ingredient. If the active constituents are insoluble in the carrier, they are dispersed in the carrier by means of, for example, a suspension, emulsion, gel, cream or paste, and the like. A preferred vehicle to act as solvent and/or diluent for the active constituents is water. Various oils, such as vegetable oils obtained from any of corn, sunflower, safflower, soybean, canola, and the like, may also be used as a vehicle, either alone or in combination. Various oils may also be used in combination with water following emulsification.

v. Humectant

Compositions under the invention may optionally comprise one or more humectants, for example:

dibutyl phthalate, gelatin, glycerin, soluble collagen, sorbitol, sodium 2-pyrrolidone-5-carboxylate A preferred humectant, under the invention, is glycerin.

vi. Emollient

Compositions under the invention may optionally comprise one or more emollients, for example, butane-1,3-diol,
cetyl palmitate,
dimethylpolysiloxane,
glyceryl monoricinoleate,
glyceryl monostearate,
isobutyl palmitate,
isocetyl stearate,
isopropyl palmitate,
isopropyl stearate,
butyl stearate,
isopropyl laurate,
hexyl laurate,
decyl oleate,
isopropyl myristate,
lauryl lactate,
octadecan-2-ol,
caprylic triglyceride
capric triglyceride
palmitic acid,
polyethylene glycol,
propane-1,2-diol,
stearic acid,
triethylene glycol,
sesame oil,
coconut oil,
safflower oil
isoamyl laurate
nonoxynol-9
panthenol
hydrogenated vegetable oil
tocopheryl acetate
tocopheryl linoleate
allantoin
propylene glycol
arachis oil,
castor oil,
isostearic acid,
palmitic acid,
isopropyl linoleate,
lauryl lactate,
myristyl lactate,
decyl oleate,
myristyl myristate.

vii. Sun Blocking Agent

The compositions, according to the invention, may optionally comprise a sun blocking agent. A preferred sun blocking agent under the invention is octyl palmitate.

viii. Anti-inflammatory Agent

The compositions, according to the invention, may optionally comprise an anti-inflammatory agent. Preferred anti-inflammatory agents, under the invention, include extracts of Aloe vera, panthenol, tocopheryl acetate, and tocopheryl linoleate.

ix. Preservative

Other than water activity depressants and antimicrobial components such as Triclosan, the compositions, according to the invention, may optionally comprise one or more preservatives such as polymethoxy bycyclic oxazolidine, methyl paraben, propyl paraben, and DMDM hydantoin.

x. Viscosity Enhancer or Thickening Agent

The compositions, according to the invention, may optionally comprise a viscosity enhancer or thickening agent. Viscosity enhancers of various classes may be chosen, including microbial polysaccharides, such as xanthan gum; cellulose derivatives, such as methylcellulose, carboxymethylcellulose, hydroxypropylmethylcellulose adn hydroxyethylcellulose; and sugar alcohols, such as sorbitol.

xi. Emulsifier

The compositions, according to the invention, may also comprise one or more emulsifiers. Preferred emulsifiers under the invention include: polysorbate-60, sorbitol, and sorbitan stearate. Such emulsifiers may be incorporated into the instant compositions singly or in any combination.

xii. Vitamins and Vitamin Derivatives

The compositions, according to the invention, may also comprise one or more ingredients which are vitamins or vitamin derivatives, other than those which may be present in other components of the instant compositions. Vitamins or vitamin derivatives may be incorporated into the compositions of the invention either singly or in an combination. Examples of vitamins or vitamin derivatives which may be included in the compositions under the invention include: tocopheryl acetate, tocopheryl linoleate, dicalcium pantothenate, and panthenol.

xiii. Surfactant

The compositions, according to the invention, may optionally comprise one or more surfactants. Surfactants used under the invention are preferably mild or very mild detergents. Preferred surfactants under the invention include: sodium laureth sulfate, and cocamide DEA.

xiv. Citric acid

The compositions according to the invention may also comprise citric acid, a naturally occurring compound present in both plant and animal cells as an intermediate of the Tricarboxylic acid cycle and in relatively high concentrations in citrus fruit. It is preferred that only plant and no animal byproducts are used. Under the invention, citric acid is preferably present in a concentration of from 0–10% by weight, more preferably from 0–5% by weight, and most preferably from 0 to about 2% by weight. The concentration of citric acid may be adjusted slightly to provide a suitable pH.

xv. Allantoin

The composition according to the invention may also comprise allantoin. Allantoin is a natural product which occurs in both plants and animals-plants being preferable here. Allantoin is considered to stimulate cell proliferation and promote healing of the skin. The allantoin component of the composition is preferably present in a concentration of from 0–5% by weight, preferably from 0.01–2% by weight.

xvi. Aloe vera components

The composition according to the invention also comprises a cosmetically and physiologically acceptable preparation obtained from the Aloe vera plant. Constituents of this plant are reported to prevent infection and to have antifungal properties. The gel obtained from Aloe vera leaves are said to be useful for any dry skin condition, being especially useful around the eyes and sensitive facial skin. The gel has also been recommended for treating fungal skin infections. The Aloe vera component of the composition is preferably present in a concentration of from 0.1–10% by weight, more preferably from 0.2–5% by weight, and most preferably from 0.5–1.5% by weight.

xvii. Natural Scents

The composition according to the invention also comprises one or more natural scents. Natural scents added to the skin care compositions under the invention impart a pleasant, mild scent, and are formulated to avoid any negative impact on the skin such as drying, irritation or allergies. For example, natural scents may be obtained from plant materials in the form of essential oils by the process of fractional distillation, thus avoiding extraction procedures involving organic solvents.

xviii. Other herbal extracts

The compositions according to the invention also comprise one or more natural herbal extracts, including matricaria extract, comfrey extract, and cucumber extract. Under the invention, natural herbal extracts are preferably present in a concentration of from 0–5% by weight, more preferably from 0–2% by weight, more preferably from 0 to about 0.8% by weight.

Medicinal use of the herb known as comfrey dates back at least to the time of the Ancient Egyptian civilization, and it has been widely used as a herbal remedy for hundreds if not thousands of years (see, for example, P. Ody (1993) *The Complete Medicinal Herbal,* Dorling Kindersley, London, New York, Stuttgart). Nicholas Culpeper, an Elizabethan herbalist listed comfrey as being amongst the most effective natural healing agents. The English physician Charles J. Macalister, M. D. used comfrey topically to treat serious skin lesions—with remarkable results (C. J. Macalister (1936) *Narrative of an Investigation Concerning an Ancient Medicinal Remedy and its Modern Utilities,* Republished 1955, The Lee Foundation for Nutritional Research, Milwaukee, Wis.). One constituent of comfrey considered to be responsible for its medicinal properties is allantoin.

Matricaria is another herb that has been used medicinally since antiquity. Among the skin conditions for which Matricaria has been recommended are: various sores and wounds, eczema and inflammation.

Without being limited by any theory of mode of action of any of these constituents, it is believed that topical use of the instant skin care compositions not only helps to maintain treated skin in a healthy condition, but also promotes healing of dry, cracked sore, or damaged skin.

ixx. pH

In the case of the skin cleanser composition, the preferred pH is in the range of 6.0 to 8.0; more preferably the pH is in the range of 6.5 to 7.5.

The preferred pH of the skin moisturizer composition is in the range of 5.0 to 8.0; more preferably the pH is in the range of 6.0 to 7.0.

In one embodiment, the composition of a skin moisturizer under the invention comprises a humectant, an emollient, an absorption enhancer, an antimicrobial agent, a vitamin or vitamin derivative, herbal extract, natural scents, and a suitable vehicle or carrier.

In a preferred embodiment, the composition of a skin moisturizer under the invention comprises, for example, the following:

- a humectant, such as glycerin;
- an absorption enhancer, antimicrobial function enhancer, lipid removal enhancer such as ceramic hydroxyapatite;
- an emollient, such as glyceryl stearate, allantoin, or nonoxynol-9;
- an antimicrobial agent, such as Triclosan;
- an anti-inflammatory agent, such as aloe vera extract, panthenol
- an emulsifier, such as polysorbate 60;
- a preservative, such as DMDM hydantoin;
- a sun block agent, such as octyl palmitate;
- a vitamin or vitamin derivative, such as tocopheryl acetate;
- a herbal extract, such as comfrey extract, or Matricaria extract;
- a natural scent, such as oil of citrus fruit;
- and a suitable vehicle, such as water.

Methods, under the invention, for preparing a skin moisturizer composition comprise the steps of formulating the constituents of each composition as four separate Phases, and subsequently combining each Phase.

The skin moisturizer composition may be formulated according to the following Example.

EXAMPLE 1

Formulation of Skin Moisturizer Composition a) Phase 1M

A suitable volume of deionized water at ambient temperature was metered into a first stainless steel vessel or tank, and the mixer was turned on. Ingredients of Phase 1M, comprising nonoxynol-9, aloe vera extract and panthenol were then added, and the mixture was slowly heated to a predetermined temperature. Preferably Phase 1M of the composition is heated to a predetermined temperature in the range of 30 to 95° C., more preferably in the range of 40 to 90° C., and most preferably in the range of 50 to 80° C. In a preferred embodiment, methyl paraben is added after heating has begun, when the temperature of Phase 1M is in the range of 30 to 95° C., more preferably when the temperature of Phase 1M is in the range of 40 to 90° C., and most preferably when the temperature of Phase 1M is in the range of 50 to 80° C.

b) Phase 2M

The ingredients of Phase 2M, comprising glycerin and ceramic hydroxyapatite, were combined in a suitable second vessel and mixed thoroughly until completely homogeneous. Phase 2M was added to the first vessel when the predetermined temperature for Phase 1M had been attained.

c) Phase 3M

The constituents of Phase 3M, comprising stearic acid, octyl palmitate, tocopheryl acetate, safflower oil, and hydrogenated vegetable oil, were combined in a stainless steel third vessel, and the mixture was heated towards a predetermined temperature. Preferably the predetermined temperature for Phase 3M is in the range of 30 to 95° C., more preferably in the range of 40 to 90° C., and most preferably in the range of 50 to 80° C.

When most of the solid constituents had melted the mixer for the third vessel was turned on. When the temperature of the contents of both the third and first vessels attained their respective predetermined temperatures, Phase 3M was added to the first or main vessel, and the contents were mixed well.

After thorough mixing, heating was discontinued and the contents of the first vessel were allowed to cool.

d) Phase 4M

The ingredients of Phase 4M, comprising tocopherol linoleate, matricaria extract and comfrey extract, were combined in a suitable fourth vessel, and heated to a predetermined temperature. Preferably the predetermined temperature for Phase 4M is in the range of 30 to 60° C., more preferably in the range of 35 to 55° C., and most preferably in the range of 40 to 55° C. When the temperature of the contents of the first vessel were at the same or a similar temperature as the predetermined temperature for phase 4, the ingredients of Phase 4 were transferred from the fourth vessel to the first vessel with thorough mixing. Heating was discontinued and the mixture was allowed to cool.

When the mixture was at a suitable temperature, preferably in the range of 20–40° C., more preferably in the range of 25–35° C., natural scent was added, and the mixture was thoroughly stirred until homogeneous.

The skin moisturizer composition of the current invention provides a smooth lotion which is white or slightly off-white in color, and has a delicate scent of citrus fruit. At a temperature of 25° C., it has a pH in the range of 6–7, a viscosity in the range of 3500–6500 and preferably 4,400–5,100 centipoise, and a specific gravity near 1.0.

In one embodiment, the composition of a skin cleanser under the invention comprises an antimicrobial agent, a viscosity enhancer, an absorption enhancer, an antimicrobial function enhancer and lipid removal enhancer, a vitamin or vitamin derivative, herbal extract, natural scent, and a suitable vehicle.

In a preferred embodiment, the composition of a skin cleanser under the invention comprises, for example, the following:

an antimicrobial agent, such as Triciosan;

an absorption enhancer, antimicrobial function enhancer, and lipid removal enhancer, such as ceramic hydroxyapatite;

an emollient, such as propylene glycol, nonoxynol-9;

an anti-inflammatory agent, such as aloe vera extract, panthenol a surfactant, such as cocamide DEA, sodium laureth sulfate;

an emulsifier, such as polysorbate 60, sorbitan stearate;

a preservative, such as propyl paraben, methyl paraben;

a sun block agent, such as octyl palmitate a vitamin or vitamin derivative, such as tocopheryl linoleate;

a herbal extract, such as comfrey extract, or matricaria extract;

a natural scent, such as oil of cucumber;

and a suitable vehicle, such as water.

Methods, under the invention, for preparing the skin cleanser composition comprise the steps of formulating the constituents of each composition as four Phases, and subsequently combining each Phase sequentially.

The skin cleanser composition may be formulated according to the following Example.

EXAMPLE 2

Formulation of Skin Cleanser Composition a) Phase 1C

A suitable volume of deionized water at ambient temperature was metered into a first stainless steel vessel or tank, and the mixer was turned on. Ingredients of Phase 1C, comprising sodium laureth sulfate aloe vera extract, citric acid and panthenol were then added, and the mixture was thoroughly stirred.

b) Phase 2C

The ingredients of Phase 2, comprising sorbitol and ceramic hydroxyapatite, were combined in a suitable second vessel and mixed thoroughly until completely homogeneous. Phase 2 was added to the first vessel.

c) Phase 3C

The constituents of Phase 3C, comprising propylene glycol, Nuocept C (Polymethoxy Bycyclic Oxazolidine) and Triclosan, were combined in a suitably sized third vessel, and the contents were thoroughly mixed. Mixing was continued and the mixture was heated until the mixture was homogeneous and it attained a predetermined temperature. Preferably the predetermined temperature for Phase 3C is in the range of 35 to 95° C., more preferably in the range of 45 to 85° C., and most preferably in the range of 55 to 75° C. Heating was discontinued and the mixture was allowed to cool. When the temperature of Phase 3C in the third vessel was in the range of 15 to 35° C., and preferably in the range of 18 to 25° C., Phase 3C was transferred to the first vessel, and the contents were mixed well.

d) Phase 4C

Mixing of the contents of the first vessel was continued while the ingredients of Phase 4C at ambient temperature, comprising nonoxynol cocamide DEA, comfrey extract, and matricaria extract, were added sequentially to the first vessel.

Finally, natural scent was added to the mixture in the first vessel, and the mixture was thoroughly stirred until homogeneous.

The skin cleanser composition of the current invention provides a smooth, viscous liquid which is clear to slightly opaque, and has a slight scent of cucumber. At a temperature of 25° C., it has a pH in the range of 6.5–7.5, a viscosity in the range of 3,000–4,000, even more preferably in the range of 3200–3800 centipoise, and a specific gravity near approximately 1.0.

A preferred embodiment of the skin moisturizer composition according to the invention comprises the constituents shown in the following Example.

EXAMPLE 3

Skin Moisturizer Composition

Phase 1 comprises:
Deionized water, to 100% w/w
Panthenol, up to 10% w/w
Methyl paraben, up to 5% w/w, and
Aloe vera extract, up to 7% w/w
Phase 2 comprises:
Glycerin, up to 10% w/w, and
Ceramic hydroxyapatite, up to 5% w/w
Phase 3 comprises:
Stearic acid, up to 10% w/w
Tocopherol acetate, up to 5% w/w
Octyl palmitate, up to 10% w/w
Safflower oil, up to 10% w/w
Hydrogenated vegetable oil, up to 10% w/w
Propyl paraben, up to 5% w/w, and
Triclosan, up to 1% w/w.
Phase 4 comprises:
Herbal extract (for example, extract of comfrey, matricaria, up to 5% W/W
Tocopheryl linoleate, up to 5% w/w, and
Allantoin, up to 5% w/w
oligosaccharides and Hydrolyzed wheat protein A further constituent of a preferred embodiment of the skin moisturizer composition is natural oil of citrus in the range of 0.01–0.1% w/w.

A preferred embodiment of the skin cleanser composition according to the invention comprises the constituents shown in the following Example.

EXAMPLE 4

Skin Cleanser Composition

Phase 1 comprises:
Deionized water, to 100% w/w

Panthenol, up to 10% w/w
Aloe vera extract, up to 7% w/w, and
Citric acid, up to 10% w/w.
Phase 2 comprises:
Sorbitol, up to 10% w/w, and
Ceramic hydroxyapatite, up to 5% w/w.
Phase 3 comprises:
Methyl paraben, up to 5% w/w
Propyl paraben, up to 5% w/w
Propylene glycol, up to 10% w/w
Disodium ethylenediaminetetraacetic acid, up to 2% w/w, and
Triclosan, up to 1% w/w.
Phase 4 comprises:
Herbal extract—for example, extract of comfrey, Matricaria up to 5% W/W
Nonoxynol-9
Hydroxypropyl methylcellulose
Wheat Oligosaccharides and Hydrolyzed wheat protein A further constituent of a preferred embodiment of the skin cleanser composition is natural oil of cucumber in the range of 0.01–0.1% w/w.

The present invention having been described in various embodiments, it will be apparent to one of ordinary skill that many modifications can be made thereto which nevertheless utilize the methods and compositions of the invention as disclosed. The scope of the invention is defined by the appended claims rather than by the embodiments presented above.

I claim:

1. A skin cleanser formulation comprising:
   (a) an effective non-irritating amount of detergent;
   (b) an effective anti-microbial amount of triclosan;
   (c) at least one herbal extract in an amount sufficient to promote a healthy skin condition;
   (d) water; and
   (e) ceramic hydroxyapatite;
   wherein the formulation is free of volatile alcohols.

2. The skin cleanser of claim 1 wherein the triclosan constitutes from about 0.001% to 5% by weight of the cleanser.

3. The skin cleanser of claim 1 wherein the cleanser contains no petroleum based product.

4. The skin cleanser of claim 1 wherein the herbal extract is selected from the group consisting of aloe vera extract, matricaria extract, comfrey extract, cucumber extract, and mixtures thereof.

5. The skin cleanser of claim 1 wherein the amount of herbal extract is less than 5% by weight of the cleanser.

6. The skin cleanser of claim 1 further comprising a member of the group consisting of an emollient, an anti-inflammatory agent, a vitamin, a preservative, a natural scent, or mixtures thereof.

7. The composition of claim 1 wherein said ceramic hydroxyapatite is chemically pure and present in an amount sufficient to serve as at least one of an excess lipid remover and an anti-microbial function enhancer.

8. The skin cleanser of claim 7 wherein the ceramic hydroxyapatite constitutes 0.001% to 10% by weight of the cleanser.

* * * * *